US008617527B1

(12) United States Patent
O'Lenick

(10) Patent No.: US 8,617,527 B1
(45) Date of Patent: Dec. 31, 2013

(54) SILICONE CITRIC ACID ESTERS

(75) Inventor: Kevin A. O'Lenick, Dacula, GA (US)

(73) Assignee: SurfaTech Corporation, Lawrenceville, GA (US)

( * ) Notice: Subject to any disclaimer, the term of this patent is extended or adjusted under 35 U.S.C. 154(b) by 226 days.

(21) Appl. No.: 13/374,338

(22) Filed: Dec. 23, 2011

Related U.S. Application Data

(63) Continuation-in-part of application No. 12/584,274, filed on Sep. 3, 2009.

(60) Provisional application No. 61/279,259, filed on Jul. 20, 2009.

(51) Int. Cl.
*A61K 8/72* (2006.01)
*A61K 8/894* (2006.01)
*A61Q 5/12* (2006.01)
*C08G 77/445* (2006.01)

(52) U.S. Cl.
CPC . *A61K 8/894* (2013.01); *A61Q 5/12* (2013.01); *C08G 77/445* (2013.01)
USPC .................................................. 424/70.11

(58) Field of Classification Search
None
See application file for complete search history.

(56) References Cited

U.S. PATENT DOCUMENTS 5,508,394 A 4/1996 Kappes et al.
2002/0166179 A1 * 11/2002 Wohlman et al. ................. 8/405

* cited by examiner

*Primary Examiner* — Brian Gulledge

(57) ABSTRACT

The current invention is drawn to a series of citrate esters having alkyl groups and a silicone groups esterified onto citric acid. This results an outstanding skin feel, making outstanding waterproofing and emollient properties when applied to skin. A required critical element of the invention is that both the silicone and the alkyl material be mono functional with regard to hydroxyl functionality. If either group has more than mono functionality, they will react with the citric acid (which has three carboxyl groups) to give undesired polymers. The ability to vary the ratio of alkyl to silicone results an ability to alter skin feel and consequently provide the cosmetic formulator with more latitude in choosing ingredients for incorporation into formulations.

20 Claims, No Drawings

SILICONE CITRIC ACID ESTERS

RELATED APPLICATIONS

This application is a continuation in part of Ser. No. 12/584,274, filed Sep. 3, 2009, which claims priority to and benefit of U.S. Provisional Application No. 61/279,259 filed Jul. 20, 2009, the disclosure of which is incorporated herein for all purposes.

FIELD OF THE INVENTION

The current invention is drawn to a series of citrate esters having alkyl groups and a silicone groups esterified onto citric acid. This results an outstanding skin feel, making outstanding waterproofing and emollient properties when applied to skin. A required critical element of the invention is that both the silicone and the alkyl material be mono functional with regard to hydroxyl functionality. If either group has more than mono functionality, they will react with the citric acid (which has three carboxyl groups) to give undesired polymers. The ability to vary the ratio of alkyl to silicone results an ability to alter skin feel and consequently provide the cosmetic formulator with more latitude in choosing ingredients for incorporation into formulations.

The compositions of the present invention are esters that are modified to have unique skin spreadability properties. This provides particular value in the personal care arena. Specifically, the esters are useful as a carrier in antiperspirants, pigmented products, skin care products, and the like since they spread rapidly and efficiently on the skin from a stiff gel providing emmoliency and a host of ester soluble additives including sun screen actives, hydroxy acids, antioxidants, flavonoids, tocopherol, vitamins and the like. They can be formulated into products to provide an appealing feel on the skin and provide a lubricious property which improve the properties of skin creams, skin care lotions, moisturizers, facial treatments such as acne or wrinkle removers, personal and facial cleansers, liquid soaps, bath oils, perfumes, colognes, sachets, sunscreens, pre-shave and after-shave lotions, shaving soaps, and shaving lathers. It can be used in hair shampoos, hair conditioners, hair sprays, mousses, permanents, depilatories, and cuticle coats, to enhance cosmetic elegance.

Citric acid is a common material of natural origin. The structure is:

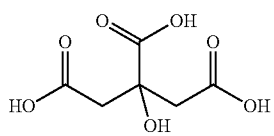 [SMILES: O=C(O)CC(O)(CC(=O)O)C(=O)O]

CAS Registry Number: 77-92-9

CA Index Name: 1,2,3-Propanetricarboxylic acid, 2-hydroxy-

Citric acid is made by fermentation, using cultures of *Aspergillus niger* are fed on a sucrose or glucose-containing medium.

Citric acid is one of a series of compounds involved in the physiological oxidation of fats, proteins, and carbohydrates to carbon dioxide and water. This series of chemical reactions is central to nearly all metabolic reactions, and is the source of two-thirds of the food-derived energy in higher organisms. Krebs received the 1953 Nobel Prize in Physiology or Medicine for the discovery. The series of reactions is known by various names, including the citric acid cycle, the Krebs cycle, and the tricarboxylic acid cycle Citrate esters are known. They conform to the following structure:

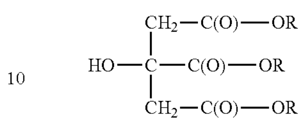

The esters are made by the reaction of fatty alcohols with citric acid.

U.S. Pat. No. 4,292,192 issued to Hooper, et al. teaches that Detergent bars for personal washing are given a deodorant property by including an ester of citric acid. The ester may be an acetyl derivative. The amount of ester used will be in the range of from about 0.3% to about 3%. Examples of the esters are triethyl citrate and acetyl tributyl citrate.

U.S. Pat. No. 2,122,716 describes long chain esters of citric acid, e.g., tridodecyl citrate, which have been used as plasticizers for resinous compositions.

U.S. Pat. Nos. 3,239,555 and 3,241,992 disclose bis-citric acid esters made by esterifying the acid groups with C1 to C18 alcohols and coupling the esters with dibasic acids. Such esters are useful as plasticizers for plastics.

U.S. Pat. No. 3,251,792, the acid groups of citric acid are esterified with alkyl, aryl, cycloalkyl and haloaryl alcohols and the hydroxyl group is esterified with a carbonyl compound. Such compounds are used as stabilizers for polypropylene.

U.S. Pat. No. 5,089,658 issued Feb. 18, 1992 to Elmore et al, is directed to citric acid esters. In one aspect, this invention pertains to citric acid esters, which contain at least one primary or secondary hydroxyl group. In another aspect, this invention relates to citric acid esters, which are reactive diluents. In still another aspect, this invention pertains to citric esters, which are pigment dispersants. The citric ester compositions of this invention are useful as reactive diluents for high solids thermosetting coating composition and as pigment dispersants for use in thermosetting coatings.

U.S. Pat. No. 4,868,236 to O'Lenick discloses a guerbet citric ester and polymers thereof useful in plastic lubrication.

None of these patents provide polyester derivatives of mixed silicone/fatty esters of citrate as envisioned by the present invention.

THE INVENTION

Objectives of the Invention

The object of present invention is to provide specific esters that can be altered to produce unique skin properties.

The method of doing this is to provide a molecule with both fatty groups and silicone groups present on the same citrate compound. The key to the performance is use mono-functional silicones as to minimize any potential for crosslinking.

Another objective of the present invention is a process for providing emolliency to the skin by applying the compositions of the present invention, The invention is also directed to application of the compounds to skin.

Other objectives will become clear as one reads the disclosure.

All temperatures disclosed herein are degrees C., All percentages are percentages by weight.

All patents referred to herein to the extent permitted are incorporated herein by reference.

SUMMARY OF THE INVENTION

The present invention is directed to a citrate ester that contains fatty portions and silicone portions making the materials amphiphilic. The ratio of fatty to silicone results in products that have very different properties. The properties that can be varied are hardness, melt point, waterproofing, spreadability and skin feel.

The higher the fatty concentration in the molecule, the better the waterproofing, the harder the ester and the less spreadable the ester. The higher the silicone content the more spreadable and the material less the waterproofing.

DETAILED DESCRIPTION OF THE INVENTION

The present invention is directed to an ester conforming to the following structure:

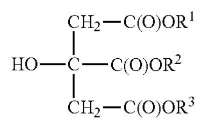

wherein:

$R^1$, $R^2$ and $R^3$ are independently a mixture of:

(a) alkyl having 8 to 22 carbon atoms; and (b) monofunctional silicone conforming to the following structure:

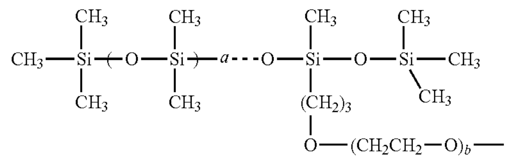

a is an integer ranging from 0 to 10;

b is an integer ranging from 0 to 20.

The esters of the current invention are made by a esterification of citric acid with a mixture of monofunctional fatty alcohol and silicone compounds.

The products of the present invention are made by the esterification reaction of:

(a) citric acid conforming to the following structure:

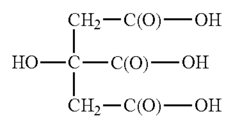

(b) a monofunctional fatty alcohol conforming to the following structure;

$$HO—(CH_2)_d—CH_3$$

d is an integer ranging from 8 to 22;

and (c) a monofunctional silicone conforming to the following structure:

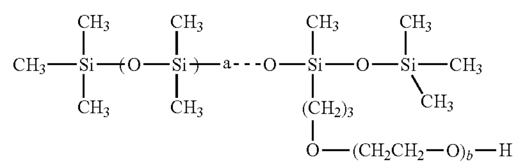

a is an integer ranging from 0 to 10;

b is an integer ranging from 0 to 20.

A required critical element of the invention is that both the silicone and the alkyl material be mono functional with regard to hydroxyl functionality. If either group has more than mono functionality, they will react with the citric acid (which has three carboxyl groups) to give undesired polymers.

PREFERRED EMBODIMENT

In a preferred embodiment a is 0.

In a preferred embodiment a is 5.

In a preferred embodiment a is 2.

In a preferred embodiment a is 10.

In a preferred embodiment said effective conditioning concentration ranges from 0.1 to 20% by weight.

In a preferred embodiment said effective conditioning concentration ranges from 1% to 10% by weight.

In a preferred embodiment said effective conditioning concentration ranges from 2% to 8% by weight.

Raw Materials

Citric Acid

Citrate is an item of commerce commercially available from a variety of sources including Pfizer. It conforms to the following structure:

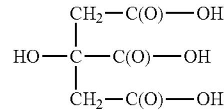

Examples 2-20 Fatty Alcohols

These acids are an item of commerce available from a variety of sources. It conforms to the following structure;

$$HO—(CH_2)_b—CH_3$$

b is an integer ranging from 5 to 23.

Fatty alcohols commercially available from a variety of sources including Condea.

| Ex | IUPAC name | Common name | CAS registry number | Molecular formula | MW |
|---|---|---|---|---|---|
| 2 | 1-Hexanol | Caproic alcohol | 111-27-3 | $C_6H_{14}O$ | 102.2 |
| 3 | 1-Heptanol | enanthic alcohol | 111-70-6 | $C_7H_{16}O$ | 116.2 |
| 4 | 1-Octanol | Caprylic alcohol | 111-87-5 | $C_8H_{18}O$ | 130.2 |
| 5 | 1-Nonanol | Pelargonic alcohol | 143-08-8 | $C_9H_{20}O$ | 144.3 |
| 6 | 1-Decanol | capric alcohol | 112-30-1 | $C_{10}H_{22}O$ | 158.3 |
| 7 | 1-Undecanol | | 112-42-5 | $C_{11}H_{24}O$ | 172.3 |
| 8 | 1-Dodecanol | lauryl alcohol | 112-53-8 | $C_{12}H_{26}O$ | 186.3 |
| 9 | 1-Tridecanol | | 112-70-9 | $C_{13}H_{28}O$ | 200.4 |

-continued

| Ex | IUPAC name | Common name | CAS registry number | Molecular formula | MW |
|---|---|---|---|---|---|
| 10 | 1-Tetradecanol | myristyl alcohol | 112-72-1 | $C_{14}H_{30}O$ | 214.4 |
| 11 | 1-Pentadecanol | | 629-76-5 | $C_{15}H_{32}O$ | 228.4 |
| 12 | 1-Hexadecanol | cetyl alcohol | 36653-82-4 | $C_{16}H_{34}O$ | 242.5 |
| 13 | 1-Heptadecanol | margaryl alcohol | 1454-85-9 | $C_{17}H_{36}O$ | 256.5 |
| 14 | 1-Octadecanol | stearyl alcohol | 112-92-5 | $C_{18}H_{38}O$ | 270.5 |
| 15 | 1-Nonadecanol | | 1454-84 | $C_{19}H_{40}O$ | 284.5 |
| 16 | 1-Eicosanol | arachidyl alcohol | 629-96-9 | $C_{20}H_{42}O$ | 298.6 |
| 17 | 1-Heneicosanol | | 15594-90-8 | $C_{21}H_{44}O$ | 312.6 |
| 18 | 1-Docosanol | behenyl alcohol | 661-19-8 | $C_{22}H_{46}O$ | 326.6 |
| 19 | 1-Tricosanol | | 3133-01-5 | $C_{23}H_{48}O$ | 340.6 |
| 20 | 1-Tetracosanol | Lignoceryl alcohol | 506-51-4 | $C_{24}H_{50}O$ | 354.7 |

In this table "b" is calculated as the number of carbon atoms − 1.

Silicones

The silicones useful in the preparation of the compounds of the present invention are available commercially from Siltech LLC, 1625 Lakes Parkway, Lawrenceville, Ga. 30043. They conform to the following structure:

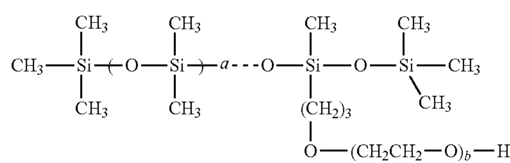

a is an integer ranging from 0 to 10;

b is an integer ranging from 0 to 20.

Example 21-30

| Example | a | b | MW* |
|---|---|---|---|
| 21 | 0 | 0 | 238 |
| 22 | 2 | 0 | 386 |
| 23 | 5 | 0 | 608 |
| 24 | 10 | 0 | 978 |
| 25 | 0 | 5 | 458 |
| 26 | 2 | 5 | 606 |
| 27 | 5 | 10 | 1048 |
| 28 | 10 | 20 | 1858 |
| 29 | 5 | 2 | 696 |

*MW is molecular weight determined on a monofunctional silicone by using the formula 56110/hydroxyl value.

Esterification Process

General Procedure

To a round bottom flask equipped with thermometer, agitation and nitrogen sparge is added the specified number of grams of alcohol (Example 2-20). The reaction mixture us heated to 160-170 C. Next 64 grams of citric is slowly added over 30 minutes under good agitation. Finally, add the specified number of grams of the specified silicone compound. Next add 0.1% by weight of all components of stannous oxylate. The temperature is increased to 170-190° C. for eight to twenty hours, water is generated and distilled off. The reaction is stopped when the water ceases to come off.

| | Fatty Alcohol | | Silicone | |
|---|---|---|---|---|
| | Example | Grams | Example | Grams |
| 31 | 11 | 228.4 | 21 | 476.0 |
| 32 | 3 | 116.2 | 22 | 772.0 |
| 33 | 4 | 130.2 | 23 | 1216.0 |
| 34 | 5 | 144.2 | 24 | 1956.0 |
| 35 | 6 | 354.7 | 25 | 916.0 |
| 36 | 7 | 344.6 | 26 | 606.6 |
| 37 | 8 | 372.6 | 27 | 1048.0 |
| 38 | 9 | 400.8 | 28 | 1858.0 |
| 39 | 10 | 428.8 | 29 | 696.0 |
| 40 | 2 | 204.4 | 29 | 696.0 |
| 41 | 12 | 703.3 | 29 | 69.6 |
| 42 | 13 | 25.6 | 29 | 2018.0 |
| 43 | 14 | 2.8 | 28 | 5202.0 |
| 44 | 15 | 142.4 | 27 | 2620.0 |
| 45 | 16 | 156.3 | 26 | 1515.0 |
| 46 | 17 | 468.9 | 25 | 687.0 |
| 47 | 18 | 489.9 | 24 | 1467.0 |
| 48 | 19 | 510.6 | 23 | 912.0 |
| 49 | 6 | 258.4 | 22 | 579.0 |

The reaction is monitored by acid value, which becomes vanishingly low during the reaction. The products are used without purification.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. An ester made by the esterification reaction of:

(a) citric acid conforming to the following structure:

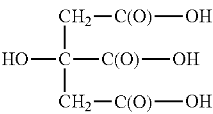

(b) a monofunctional fatty alcohol conforming to the following structure;

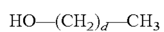

d is an integer ranging from 8 to 22;

and (c) a monofunctional silicone conforming to the following structure

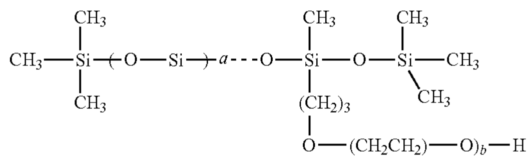

a is an integer ranging from 0 to 10;

b is an integer ranging from 0 to 20.

2. An ester of claim 1 wherein a is 0.

3. An ester of claim 1 wherein a is 5.

4. An ester of claim 1 wherein a is 2.

5. An ester of claim 1 wherein a is 10.

6. A process for conditioning hair and skin which comprises contacting the hair or skin with an effective conditioning concentration of a polyester made by the esterification reaction of:

(a) citric acid conforming to the following structure:

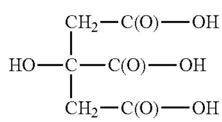

(b) a monofunctional fatty alcohol conforming to the following structure;

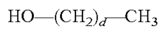

d is an integer ranging from 8 to 22;

and (c) a monofunctional silicone conforming to the following structure:

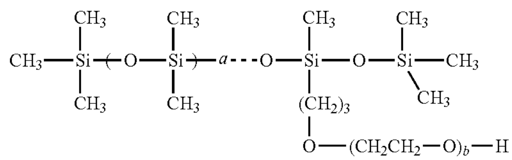

a is an integer ranging from 0 to 10;

b is an integer ranging from 0 to 20.

7. A process of claim 6 wherein said effective conditioning concentration ranges from 0.1 to 20% by weight.

8. A process of claim 6 wherein said effective conditioning concentration ranges from 1% to 10% by weight.

9. A process of claim 6 wherein a is 0.

10. A process of claim 6 wherein a is 5.

11. A process of claim 6 wherein a is 2.

12. A process of claim 6 wherein a is 10.

13. A process of claim 7 wherein a is 0.

14. A process of claim 7 wherein a is 5.

15. A process of claim 7 wherein a is 2.

16. A process of claim 7 wherein a is 10.

17. A process of claim 8 wherein a is 0.

18. A process of claim 8 wherein a is 5.

19. A process of claim 8 wherein a is 2.

20. A process of claim 8 wherein a is 10.

* * * * *

UNITED STATES PATENT AND TRADEMARK OFFICE
CERTIFICATE OF CORRECTION

PATENT NO. : 8,617,527 B1
APPLICATION NO. : 13/374338
DATED : December 31, 2013
INVENTOR(S) : Kevin A. O'Lenick It is certified that error appears in the above-identified patent and that said Letters Patent is hereby corrected as shown below:

In the Claims:

Col. 6 Line 58 delete

“ 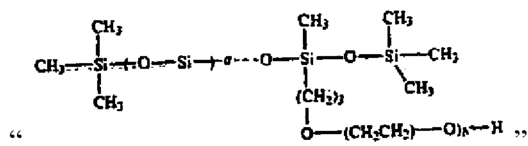 ”

and insert

-- 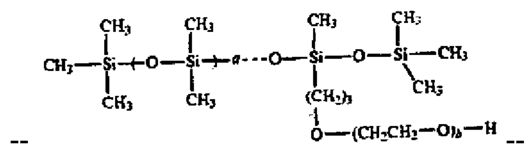 --

Signed and Sealed this
Fifteenth Day of April, 2014

Michelle K. Lee
*Deputy Director of the United States Patent and Trademark Office*